United States Patent [19]
Seman et al.

[11] Patent Number: 5,314,999
[45] Date of Patent: May 24, 1994

[54] DERIVATIVES OF BASIC POLYENE MACROLIDES AND THEIR PREPARATION

[75] Inventors: Michel Seman, Paris; Jean F. Nicolay, Arcachon, both of France

[73] Assignees: Laboratoires Mayoly-Spindler, Chatou; Michel Seman, Paris, both of France

[21] Appl. No.: 612,474

[22] Filed: Nov. 14, 1990

[30] Foreign Application Priority Data

Nov. 14, 1989 [FR] France .................................. 89 14922

[51] Int. Cl.$^5$ ...................... C07H 17/08; C07H 15/24
[52] U.S. Cl. ..................................... 536/6.5; 536/18.1
[58] Field of Search ................... 536/18.1, 6.5; 514/31, 514/33, 34

[56] References Cited

U.S. PATENT DOCUMENTS 4,195,172  3/1980  Falkowski et al. ................. 536/18.1

OTHER PUBLICATIONS

Polish Journal of Chemistry, vol. 56, 1982, pp. 123–130, L. Falkowski, et al., "The Structure of N–Glycosyl Derivatives of Polyene Macrolide Antibiotics, The Reaction of Nystatin with D–Glucose".

Biochemical Pharmacology, vol. 37, No. 5, 1988, pp. 827–836, M. Cheron, et al., "Quantitative Structure–Activity Relationships in Amphotericin B Derivatives".

Guthrie et al, An Introduction to the Chemistry of the Carbohydrates, 3rd Ed., 1968, Clarendon Press, pp. 73–74.

Falkowski et al., Polish Journal of Chemistry, vol. 56, pp. 123–130 (1982).

Primary Examiner—Johnnie R. Brown
Assistant Examiner—James O. Wilson
Attorney, Agent, or Firm—Oblon, Spivak, McClelland, Maier & Neustadt

[57] ABSTRACT

The present invention relates to basic polyene macrolide derivatives, characterized in that they comprise a basic polyene macrolide which is N-substituted by a 1-amino-1-deoxyketose group which in turn is substituted or unsubstituted, to a process for their preparation and to their use for obtaining drugs.

11 Claims, 4 Drawing Sheets

DERIVATIVES OF BASIC POLYENE MACROLIDES AND THEIR PREPARATION

STATEMENT OF THE INVENTION

The present invention relates to novel soluble and non-toxic derivatives of basic polyene macrolides and in particular to novel 1-amino-1-deoxyketoses. It also relates to a process for the preparation of these derivatives and to their use as drugs.

BACKGROUND OF THE INVENTION

Polyene macrolides are a class of antifungal antibiotics which show a broad spectrum of activity in man against fungi and yeast pathogens. This is especially true of amphotericine B (AmB), which is an antifungal agent with a broad spectrum of fungistatic and fungicidal activity: *Candida albicans, Coccidiöides immitis,* Sporotrichum, *Cryptococcus neoformans,* Histoplasma, Blastomyces, *Rhizopus orizae, Aspergillus niger,* etc. Despite the introduction of imidazoles, they still remain the most efficient drug against quite a number of conditions.

Furthermore, AmB has immunomodulating properties in mice and, to a certain degree, in man. It also enhances the activity of a certain number of anti-cancer drugs.

However, due to its macrocyclic nature and amphoteric character, the AmB which corresponds to the formula A below:

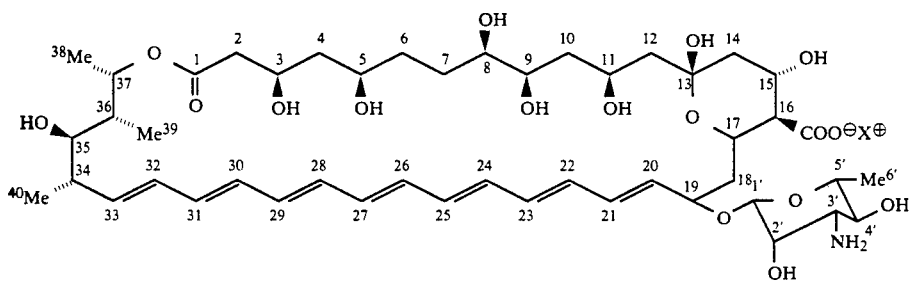

is sparingly soluble in water and tends to form micelles in aqueous solution. Moreover, the toxicity of AmB towards animal cells and in particular kidney cells, lymphocytes and erythrocytes, imposes extreme precautions when using it clinically. This is especially the case for the treatment of deep-seated and systemic mycoses which have to be treated by intravenous administration.

These considerations have led many researchers to search for non-toxic and more soluble derivatives. Accordingly, a large number of derivatives have been produced which are modified either at the level of the acid function on C16 or at the level of the primary amine function on C3'. The work of the following authors may be mentioned in particular:

BRUZZESE et al., J. Pharm. sci. (1975), 64, 462: esterification of the carboxyl group;
FALKOWSKI et al., German Patent No. 3,013,631: amidation of the carboxyl group;
WRIGHT, U.S. Pat. No. 4,272,525: esterification of the carboxyl group and substitution of the amine on C3' by aminated acids;
SCHAFFNER and BOROWSKI Antib. & Chemo. (1961), II, 724: acetylation of the amine;
SIPOS and KESELSKI, U.S. Pat. No. 4,235,993: substitution of the amine group by a benzyl group;
KULBAKH et al., U.S. Pat. No. 4,007,166: formation of an N-methyl-D-glucaminemacrolide complex;
FALKOWSKI et al., U.S. Pat. No. 4,195,172, British Patent No. 1,387,187: reaction of glycol with the amine group.

Attempts have also been made to increase the solubility of amphotericine B by adding surface-active agents or by forming salts (European Patent 31,722). Unfortunately, all these attempts have resulted in derivatives which are unstable in solution or in derivatives which have lost their antibiotic properties.

DESCRIPTION OF THE INVENTION

Figure 1:
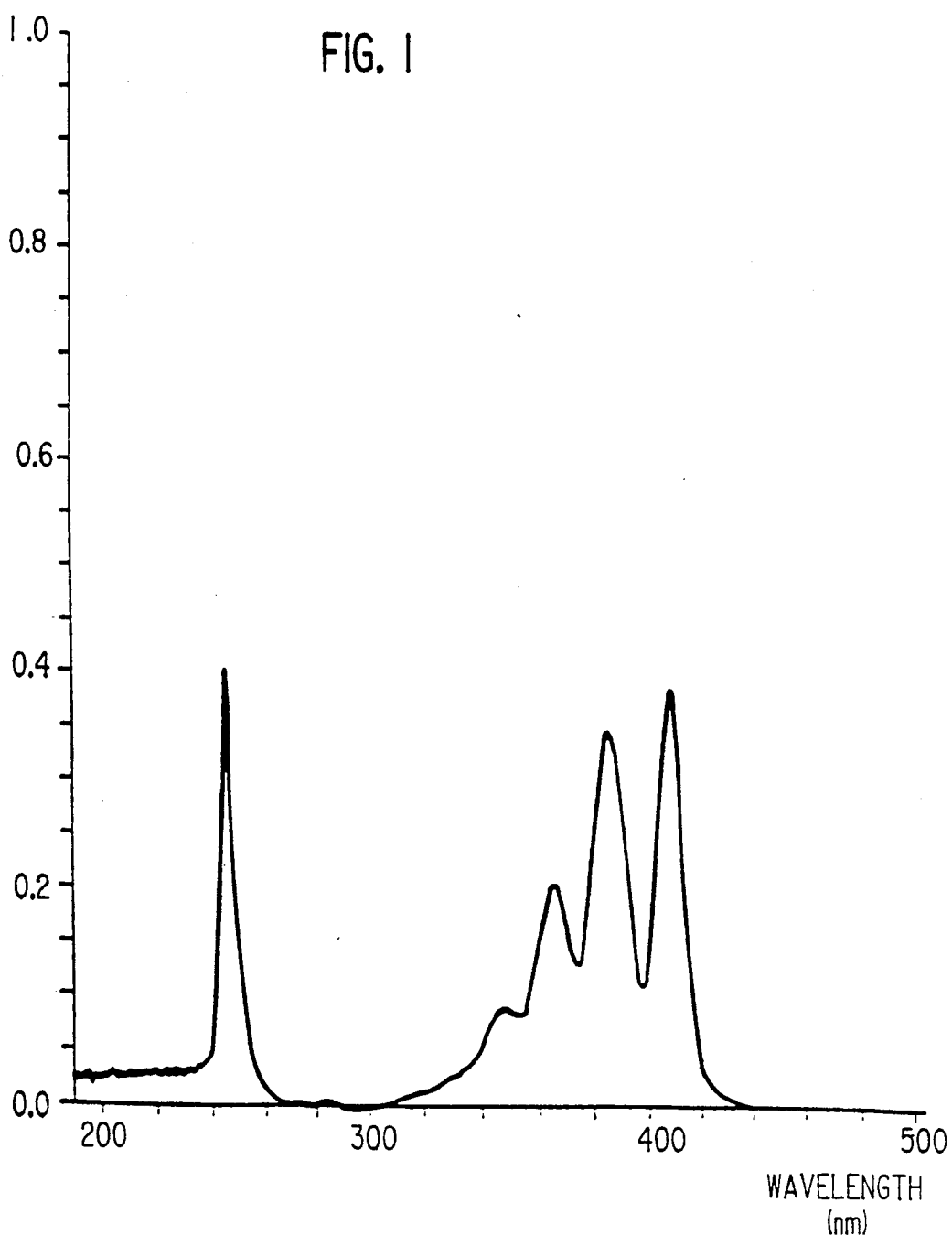
FIG. 1 shows the UV spectrum of the compound AmB 12 F prepared in Example 14.

The present invention has therefore set itself the object of providing novel derivatives of basic polyene macrolides and especially of AmB which meet the requirements in practice better than the previously known derivatives by virtue of the fact that they are soluble, slightly or not at all toxic, that they retain the amphoteric character of AmB and that they are stable in aqueous medium. It has been known for a long time (Amadori, 1925) that glycosylamines are converted in acid medium into 1-amino-1-deoxyketoses. The same compounds can be obtained directly from a sugar and an amine in the presence of a suitable catalyst according to scheme B:

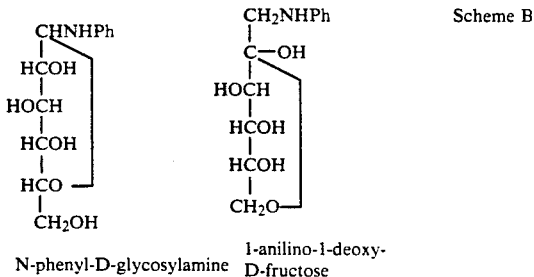

Scheme B

This so-called Amadori rearrangement has been described in more detail in Adv. Carbohydr. Chem. (1955), 10, 169. In their research into original derivatives which are soluble, have low toxicity and retain their stability in aqueous solution, the inventors noted that in the condensation reaction of a sugar with the primary amine function of the macrolide mycosamine (which has been attempted and carried out by various researchers), the nature of the condensed sugar played an essential role in the solubility and the stability of the derivatives obtained. Although the different sugars used are in theory all capable of forming a glycosylamine with AmB, it became apparent that the properties of solubility, stability and the biological properties depended on the ability of the glycosylamine thus formed to undergo an Amadori rearrangement.

The present invention relates to novel derivatives of basic polyene macrolides, characterized in that they comprise a basic polyene macrolide N-substituted by a 1-amino-1-deoxyketose group which in turn is substituted.

In the context of the present invention, a 1-amino-1-deoxyketose group is understood to mean any group resulting from the condensation of a reducing sugar which is substituted or unsubstituted with an amine function and having a characteristic beta-aminoketone functionality.

According to a preferred embodiment of the derivatives according to the invention, they correspond to the general formula I below:

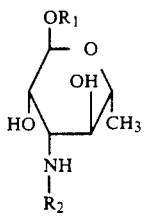

in which:
$R_1$ denotes the macrocyclic part of a polyene macrolide and
$R_2$ represents:
a structure corresponding to the formula (a) below:

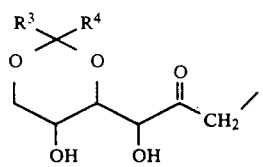

in which $R_3$ represents a hydrogen atom or a methyl group, and $R_4$ represents a hydrogen atom, a methyl, trichloromethyl, tert.-butyl, propyl, benzyl or phenyl group, or a phenyl group substituted by one or more methoxy, nitro or phosphate groups, or, alternatively, $R_3$ and $R_4$ are the linking units of a cycloalkyl group, or, alternatively,
a structure b corresponding to the formula below:

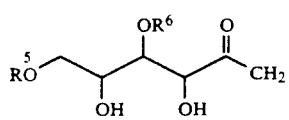

in which $R_5$ and $R_6$ are alkyl, aryl, or acyl groups, or, alternatively, a structure corresponding to the formula c below

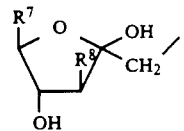

in which $R_7$ is an electron-withdrawing group, such as a carboxyl, ester, acyl, amide, nitrile or trihalogenomethyl group, or is a heterocyclic group, and $R_8$ is a hydroxyl group, an amino group, or a mercapto group, or, alternatively,
a structure of the formula d below, in which $R_9$, $R_{10}$, $R_{11}$ represent alkyl, acyl or aryl groups, and $R_{12}$ represents a hydroxyl, amino or alkoxy group,

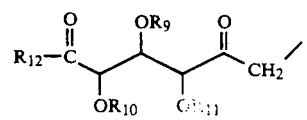

or, alternatively,
a disaccharide.

As the substituents for the substituted 1-amino-1-deoxyketose group there is present one or more of the following: a group of the formula

replacing hydrogens of two different hydroxyl groups of the ketose, where $R^3$ represents a hydrogen atom or a methyl group, and $R^4$ represents a hydrogen, a methyl, trichloromethyl, tert-butyl, propyl, benzyl or phenyl group, or a phenyl group substituted by one or more methoxy, nitro or phosphate groups or, alternatively, $R_3$ and $R_4$ are the linking units of a cycloalkyl group, or an alkyl, aryl, or acyl group replacing a hydrogen of a hydroxyl group of the ketose, or an electron-withdrawing group, such as carboxyl, ester, acyl, amide, nitrile, trihalogenomethyl, heterocyclic, amino or mercapto group replacing a hydroxyl group of the ketose.

In particular the following substituents are exemplified: methyl-benzylidine, benzylidene, ethylidene, a methyl replacing hydrogen attached to oxygen and —N—acetyl, —COOH,—CONH$_2$, and —NH$_2$ attached to carbon and replacing —OH of the 1-amino-1-deoxyketose group.

Advantageously, the 1-amino-1-deoxyketoses according to the present invention, in contrast to the glycosylamines described in the abovementioned prior art which hydrolyze rapidly in water, are stable in neutral and acidic aqueous medium, and have
very satisfying solubilizing or dispersing properties in water
the biological properties of the starting glycosylamine
and a reduced cytotoxicity with respect to that of the starting glycosylamine.

The derivatives according to the invention can be obtained in the form of mixed salts whose nature depends on the catalyst chosen for the rearrangement or on the procedure of a step of substituting the mixed salt obtained by another salt, following the said rearrangement.

According to a preferred embodiment, the 1-amino-1-deoxyketoses according to the invention are in the form of salts of the Brönsted acid used for the rearrangement.

According to a particularly advantageous variation of this embodiment, the 1-amino-1-deoxyketoses are in the form of mixed salts of oxalate and ammonium.

According to another preferred embodiment of the invention, the 1-amino-1-deoxyketoses are in the form of N-methylglucosamine salts.

The present invention also relates to a process for the preparation of the derivatives of basic polyene macrolides according to the invention, characterized in that during a first step a glycosylamine is formed by condensation of the amine function of the macrolide with the anomeric carbon of a reducing sugar, and in that during a second step the glycosylamine obtained is rearranged in an anhydrous acidic medium to form a 1-amino-1-deoxyketose having a characteristic beta-amino-ketone functionality, and in that during a third step the 1-amino-1-deoxyketose obtained is separated from the reaction medium.

According to another embodiment of the process provided by the invention, the condensation step takes place with the exclusion of light, under inert atmosphere and in an anhydrous solvent, and at a temperature between 35° C. and 50° C.

According to yet another embodiment of the process provided by the invention, the rearrangement step is induced by the addition of a catalyst selected from the group comprising Brönsted acids, such as, for example, oxalic acid or acetic acid, and the so-called "active methylene" catalysts, such as, for example, ethyl malonate or 2,4-pentanedione.

According to a preferred variation of this embodiment, the separation of the derivative obtained is effected by adding an aqueous ammonium sulphate solution.

According to another preferred variation of this embodiment, the mixed salt obtained can advantageously be substituted by another salt. The mixed salt is suspended in methanol, an aqueous solution containing 1 to 3 equivalents of acid or base is then added volume by volume. By adding 3 volumes of butanol, the water can then be removed azeotropically and the product recovered in crystalline form.

The present invention also relates to novel drugs, characterized in that they contain as active component at least one of the macrolide derivatives according to the present invention.

Apart from the above arrangements, the invention comprises other arrangements which will become evident from the remainder of the description which follows.

However, it goes without saying that these preparation examples, and pharmacological tests and studies are given solely by way of an illustration of the subject of the invention, of which they represent no limitation whatsoever.

EXAMPLES FOR THE PREPARATION OF MACROLIDE DERIVATIVES OF THE GENERAL FORMULA I ACCORDING TO THE INVENTION

EXAMPLE 1: Preparation of a mixed oxalate and ammonium salt of 1-amino-1-deoxy-4,6-O-methylbenzylidene-D-fructosyl-AmB (AmB40G)

Formula IV : 1-Amino-1-deoxy-4,6-O-methylbenzylidene-D-fructose-AmB

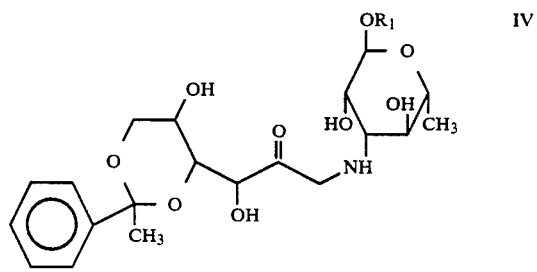

AmB is suspended in dimethylformamide (anhydrous, freshly distilled) with the exclusion of light, under an inert atmosphere and under strictly anhydrous conditions. 1.5 equivalents of 4,6-O-methylbenzylidene-D-glucopyranose are added all at once with magnetic stirring. The temperature of the mixture is brought to 38° C., and stirring is continued for a period ranging from 3 hours to 12 hours. When the solution is entirely clear, the catalyst is added (one equivalent if it is a Brönsted acid, such as oxalic acid, 10% by volume in the case of an "active methylene catalyst", and heating of the mixture is continued for 24 hours. The mixture is then cooled, and the 1-amino-1-deoxy-4,6-O-methylbenzylidene-D-fructosyl-AmB is precipitated by dropwise addition of a 10% ammonium sulphate solution in water with stirring. The precipitation is brought to completion by keeping the suspension at 4° C. for 2 hours. A light yellow crystalline product is then recovered (after centrifugation and removal of the supernatant), which is washed twice with water (or an acetone/water mixture) so as to remove the excess starting carbohydrate and any trace of solvent.

Example 2: Preparation of the N-methylglucosamine salt of 1-amino-1-deoxy-4,6-O-methylbenzylidene-D-fructosyl-AmB (AmB40F)

The N-methylglucosamine salt of the carboxyl function of this derivative is prepared by suspending the final product of Example 1 in methanol and adding 2 equivalents of a polyhydroxylated base (N-methylglucosamine) dissolved in a volume of water equivalent to that of methanol. The mixture rapidly becomes clear, and 3 volumes of an entrainer (n-butanol) are then added. The mixture is evaporated under reduced pressure until the methanol and the water have been removed. The derivative slowly crystallizes in the remaining butanol, and the suspension is left at 4° C. After centrifugation, the product is recovered, washed twice with butanol, then twice with ether. The derivative is finally dried under a high vacuum.

Example 3: Preparation of the mixed oxalate and ammonium salt of 1-amino-1-deoxy-4,6-dimethoxyfructosyl-AmB (AmB42G)

Formula V : 1-Amino-1-deoxy-4,6-dimethoxyfructosyl-AmB

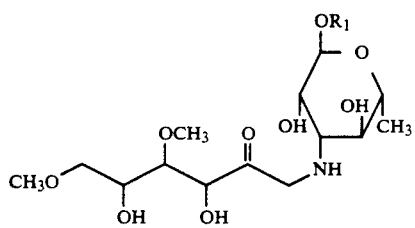

The procedure of obtaining this salt is similar to that used in Example 1, except that the carbohydrate coupled with the macrolide is 4,6di-O-methyl-D-glucopyranose.

Example 4: Preparation of the N-methylglucosamine salt of 1-amino-1-deoxy-4,6-dimethoxyfructosyl-AmB (AmB42F)

The N-methylglucosamine salt of the acid function of this derivative is prepared by suspending the final product of Example 3 in methanol and then following the procedure described in Example 2.

Example 5: Preparation of the mixed oxalate and ammonium salt of 1-deoxy-1-amino-4,6O-benzylidene-D-fructosyl-AmB (AmB20G)

Formula VI : 1-Deoxy-1-amino-4,6-O-benzylidene-D-fructosyl-AmB

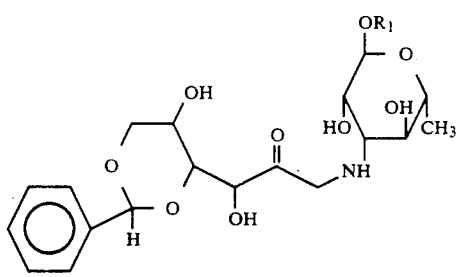

The procedure used for preparing this salt is similar to that used in Example 1, except that the carbohydrate coupled to the macrolide is 4,6-O-benzylidene-D-glucopyranose.

Example 6: Preparation of the N-methylglucosamine salt of 1-deoxy-1-amino-4,6-O-benzylidene-D-fructosyl-AmB (AmB20F)

The N-methylglucosamine salt of the acid function of this derivative is prepared by suspending the final product of Example 5 in methanol, and then following the procedure described in Example 2.

Example 7: Preparation of the mixed oxalate and ammonium salt of 1-deoxy-1-amino-4,6-O-ethylidene-D-fructosyl-AmB (AmB22G)

Formula VII : 1-Deoxy-1-amino-4,6-O-ethylidene-D-fructosyl-AmB

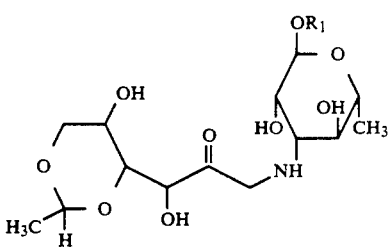

The procedure used for preparing this salt is similar to that used in Example 1, except that the carbohydrate coupled to the macrolide is 4,6-O-ethylidene-D-glucopyranose.

Example 8: Preparation of the N-methylglucosamine salt of 1-deoxy-1-amino-4,6-O-ethylidene-D-fructosyl-AmB (AmB22F)

The N-methylglucosamine salt of the acid function of this derivative is prepared by suspending the final product of Example 7 in methanol, and then following the procedure described in Example 2.

Example 9: Preparation of the mixed oxalate and ammonium salts of 6-deoxy-6-N-acetyl-1-deoxy-1-amino-fructosyl-AmB (AmB23G)

Formula VIII : 6-Deoxy-6-N-acetyl-1-deoxy-1-aminofructosyl-AmB

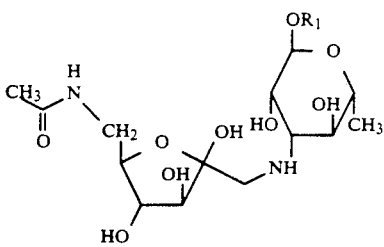

The procedure used for preparing this salt is similar to that used in Example 1, except that the carbohydrate coupled to the macrolide is 6-deoxy-6-N-acetyl-D-glucopyranose.

Example 10: Preparation of the N-methylglucosamine salt of 6-deoxy-6-N-acetyl-1-deoxy-1-aminofructosyl-AmB (Amb23F)

The N-methylglucosamine salt of the acid function of this derivative is prepared by suspending the final product of Example 9 in methanol, and then following the procedure described in Example 2.

Example 11: Preparation of the mixed oxalate and ammonium salts of 1-amino-1-deoxy-D-arabinoglucuronyl-AmB by condensation of D-glucurono-6,3-lactone with AmB (AmB17G)

Formula IX : 1-Amino-1-deoxy-D-arabinoglucuronyl-AmB

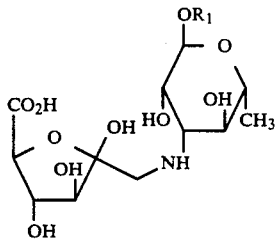

The procedure used for preparing this salt is similar to that used in Example 1, except that the carbohydrate coupled to the macrolide is D-glucurono-6,3-lactone.

Example 12: Preparation of the N-methylglucosamine salt of 1-amino-1-deoxy-D-arabinoglucuronyl-AmB by condensation of D-Glucurono-6,3-lactone with AmB (AmB17F)

The N-methylglucosamine salt of the acid function of this derivative is prepared by suspending the final product of Example 11 in methanol, and then following the procedure described in Example 2.

Example 13: preparation of the mixed oxalate and ammonium salts of 1-amino-1-deoxy-D-arabinoglucuronamidyl-AmB (AmB 12 G)

Formula X : 1-amino-1-deoxy-D-arabinoglucuronamidyl-AmB

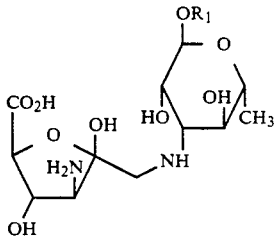

The procedure used for preparing this salt is similar to that used in Example 1, except that the carbohydrate coupled to the macrolide is glucuronamide.

Example 14: Preparation of the N-methylglucosamine salt of 1-amino-1-deoxy-D-arabinoglucuronamidyl-AmB (AmB 12 F)

The N-methylglucosamine salt of the acid function of this derivative is prepared by suspending the final product of Example 13 in methanol, and then following the procedure described in Example 2.

Example 15: Preparation of the mixed oxalate and ammonium salts of 1,3-diamino-1,3-dideoxy-D-arabinoglucuronamidyl-AmB (AmB50G)

Formula XI :
1,3-Diamino-1,3-dideoxy-D-arabinoglucuronamidyl-AmB

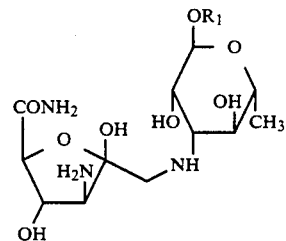

The procedure used for preparing this salt is similar to that used in Example 1, except that the carbohydrate coupled to the macrolide is 3-amino-3-deoxy-D-glucurono-6,3-lactam.

Example 16: Preparation of the N-methylglucosamine salt of 1,3-diamino-1,3-dideoxy-D-arabinoglucuronamidyl-AmB (AmB50F)

The N-methylglucosamine salt of the acid function of this derivative is prepared by suspending the final product of Example 15 in methanol, and then following the procedure described in Example 2.

Example 17: Preparation of the mixed oxalate and ammonium salts of 1-amino-1-deoxy-D-arabinoglucuronyl-AmB (AmB17G) by condensation of glucuronic acid with AmB The procedure used for preparing this salt is similar to that used in Example 1, except that the carbohydrate coupled to the macrolide is D-glucuronic acid. The product obtained is identical to that of Example 11.

ACCOUNT OF THE MICROBIOLOGICAL AND TOXICOLOGICAL STUDIES CARRIED OUT AS PROOF OF THE THERAPEUTIC PROPERTIES OF THE AmB DERIVATIVES OF THE GENERAL FORMULA I

A) MICROBIOLOGICAL STUDIES

A.1 : Study of the antibiotic efficiency of AmB derivatives in liquid medium against different yeasts The antibiotic efficiency was tested by the growth inhibition method in liquid medium (Sabouraud broth) in the presence of different concentrations of the derivatives studied.

A yeast suspension was cultivated in a broth in such a manner that about $1 \times 10^2$ cell/ml were obtained.

The tubes containing the different concentrations of antifungal substance were inoculated with the same amount of yeast cells, and were then incubated at 28° C. for 18 hours with stirring. For each concentration of antifungal substance, two identical tubes were prepared.

The inhibition of fungal growth corresponding to the different concentrations was evaluated for each molecule by spectrophotometry at 620 nm and expressed in percent with respect to a reference solution without antifungal substance.

A.2 : Study of the antibiotic efficiency of amphotericine B derivatives in agar-agar medium against Aspergillus The antibiotic activity was tested by the diffusion method in agar-agar medium (Sabouraud agar-agar).

The efficiency of each molecule was determined by the size of the growth-inhibiting zone around a WHATMAN 3M paper disc impregnated with the antibiotic substance of a given concentration.

A suspension of Aspergillus spores in a broth was prepared, 0.2 ml of this suspension was used to inoculate at its surface an agar-agar medium which was solidified in such a manner that a homogeneous growth layer was obtained. After spreading, the WHATMAN 3M paper discs (diameter: 1 cm) were placed on the surface of the agar-agar, and then impregnated with 0.1 ml of the antibiotic substance at different concentrations.

The doses giving a 50% inhibition of the growth of the species S. cerevisiae, C. neoformans, P. orbiculare, C. albicans, C. albicans B 2630, and the doses giving a growth-inhibiting zone of the species A. flavus and A. fumigatus of 1 cm around a disc placed in the middle of the solid culture, determined in both cases using the derivatives 12, 17, 20, 22 and 23 of series G and F, are shown in Tables 1 and 1A below. These tables show that the AmB derivatives prepared according to the invention hence retain the antibiotic properties of the molecule from which they originated, namely AmB.

TABLE 1

ANTIFUNGAL IN VITRO ACTIVITY OF THE AmB DERIVATIVES AGAINST DIFFERENT SPECIES OF FUNGI: COMPARISON OF THE SALTS WITH THE DIFFERENT AmB DERIVATIVES IC 50 in molarity*

| DERIVATIVES | Saccharomyces cerevisiae | Cryptoccocus neoformans | Pytirosporum orbiculare |
|---|---|---|---|
| FUGIZONE++ | N.D. | $5 \times 10^{-8}$ | $1.5\ 10^{-8}$ |
| AmB* | $5.4 \times 10^{-7}$ | $8 \times 10^{-8}$ | $<10^{-8}$ |
| F series | | | |
| AmB 12 | $1.1 \times 10^{-6}$ | $6.5 \times 10^{-8}$ | $9.6 \times 10^{-8}$ |
| AmB 17 | $1.4 \times 10^{-6}$ | $1.5 \times 10^{-7}$ | $9 \times 10^{-8}$ |
| AmB 20 | $1.1 \times 10^{-6}$ | $4.5 \times 10^{-8}$ | $1 \times 10^{-7}$ |
| AmB 22 | $1.6 \times 10^{-6}$ | $2.5 \times 10^{-7}$ | $1.8 \times 10^{-7}$ |
| AmB 23 | $1.6 \times 10^{-6}$ | $1.5 \times 10^{-7}$ | $7.6 \times 10^{-8}$ |
| G series | | | |
| AmB 12 | $6.2 \times 10^{-7}$ | $8 \times 10\ 8$ | N.D. |
| AmB 17 | $8.6 \times 10^{-7}$ | $6 \times 10^{-8}$ | N.D. |
| AmB 20 | $1 \times 10^{-6}$ | $6 \times 10^{-8}$ | N.D. |
| AmB 22 | $1.2 \times 10^{-6}$ | $1.2 \times 10^{-7}$ | N.D. |
| AmB 23 | $1 \times 10^{-6}$ | $1.7 \times 10^{-7}$ | N.D |

TABLE 1A

ANTIFUNGAL IN VITRO ACTIVITY OF THE AmB DERIVATIVES AGAINST DIFFERENT SPECIES OF FUNGI: COMPARISON OF THE SALTS WITH THE DIFFERENT AmB DERIVATIVES IC 50 in molarity*

| DERIVATIVES | Candida albicans | Candida albicans B 2630 | Aspergillus** flavus | Aspergillus** fumigatus |
|---|---|---|---|---|
| FUGIZONE | $1.9 \times 10^{-8}$ | $8 \times 10^{-8}$ | N.D | N.D. |
| AmB* | $8 \times 10^{-8}$ | $3.5 \times 10^{-7}$ | $5 \times 10^{-5}$ | $5 \times 10^{-5}$ |
| F series | | | | |
| AmB 12 | $9 \times 10^{-8}$ | $2.4 \times 10^{-7}$ | $3 \times 10^{-4}$ | $8 \times 10^{-5}$ |
| AmB 17 | $1.3 \times 10^{-7}$ | N.D. | $2 \times 10^{-4}$ | $2 \times 10^{-4}$ |
| Amb 20 | $8.5 \times 10^{-8}$ | $1.5 \times 10^{-7}$ | $1.5 \times 10^{-4}$ | $2 \times 10^{-4}$ |
| AmB 22 | $5.6 \times 10^{-7}$ | N.D. | $1.5 \times 10^{-4}$ | $5 \times 10^{-4}$ |
| AmB 23 | $4 \times 10^{-7}$ | N.D. | $6 \times 10^{-4}$ | $2 \times 10^{-4}$ |
| G series | | | | |
| AmB 12 | $1 \times 10^{-7}$ | N.D. | $9 \times 10^{-5}$ | $1 \times 10^{-4}$ |
| AmB 17 | $1.2 \times 10^{-7}$ | N.D. | $9 \times 10^{-5}$ | $3.5 \times 10^{-5}$ |
| AmB 20 | $1 \times 10^{-7}$ | N.D. | $6 \times 10^{-4}$ | $1.3 \times 10^{-4}$ |
| AmB 22 | $9 \times 10^{-8}$ | N.D | $9 \times 10^{-5}$ | $1 \times 10^{-4}$ |
| AmB 23 | $1\ 10^{-7}$ | N.D. | $5 \times 10^{-4}$ | $9 \times 10^{-5}$ |

Tables 1 and 1A
F series: Catalysis by oxalic acid, NMG salt
G series: Catalysis by oxalic acid, mixed ammonium and oxalate salt
*IC 50 = growth-inhibiting concentration of 50% of the bacteria
*AmB dissolved in a 5% glucose solution
**concentration giving a growth inhibition of 1 cm around a disc in solid medium
++registered trademark

B) TOXICOLOGICAL STUDIES

The toxic properties of the derivatives were studied on human and mouse red corpuscles and on lymph cells of peripheral blood from bone marrow and human thymus, on T and B spherical lymphocytes from mice and on two tumour strains: XG3 (mouse), Daudi (man).

B.1: Study of the toxicity on red corpuscles

All the solutions of the AmB derivatives according to the invention were prepared immediately before use by diluting 4 mg of substance in 100 $\mu l$ of 5% glucose solution, and then, after 15 minutes protected from light, 100 $\mu l$ of sterile distilled water are added, and the mixture is made up to stock solutions of 4 mg/ml with a 5% glucose solution. For comparative study of the effects of AmB, 4 mg of FUNGIZONE are diluted with 1 ml of 5% glucose.

The cells are prepared by placing 1 ml of a peripheral blood sample into a tube together with Ficollhypaque to remove the lymphocytes, and then centrifuging the mixture at 2000 rpm for 20 minutes. The remaining red corpuscles are recovered, washed once with 0.9% NaCl and then twice with 150 Mm KCl, 0.5 Mm tris-HCl, pH 7.4.

A 1.25% suspension is then prepared with 150 mM KCl solution, 0.5 mM tris-HCl, pH 7.4, and 150 $\mu l$ thereof are distributed in wells along with 50 $\mu l$ of each of the dilutions of the derivatives, plus a control well (5% glucose solution).

The cells are then incubated at 37° C. in a steam cabinet for 1 hour 30.

To evaluate the cell lysis, haemoglobin is essayed by removing 100 $\mu l$ of the supernatant in each well and diluting the sample with 1 ml of distilled water.

The haemoglobin concentration is calculated by measuring the optical density at 540 nm and taking into account the absorption of the derivatives of amphotericine B.

LD 50 is the dose which leads to lysis in 50% of the erythrocytes (a control of 100% lysis is obtained with distilled water, and reference lysis of 0% is obtained with the 5% glucose solution).

B.2: Study of the toxicity on nucleated cells

The solutions of the amphotericine B derivatives are prepared similarly to those mentioned in paragraph B.1.

The cells are prepared by placing 20 ml of blood diluted to ½ with 0.9% NaCl into a tube together with 10 ml of Ficoll-hypaque, and the mixture is centrifuged at 2000 rpm for 30 minutes. The cell nuclei are recovered and washed twice with PBS buffer containing 5% of foetal calf serum.

The cells are prepared by suspending $1.14 \times 10^6$ cells/ml in RPMI 1640 containing 2.5% of foetal calf serum and by filling each well with 150 μl. 50 μl of each dilution of the derivatives are added and also one control (5% glucose solution).

The cells are then incubated in a steam cabinet at a $CO_2$ concentration of 5% for 1 hour 30 at 37° C. or at ambient temperature.

To evaluate the toxicity of the derivatives, a cell count in the presence of trypan blue is made, and the LD 50 (concentration of the derivative leading to a mortality of 50%) is calculated with respect to the control (5% glucose solution) for each concentration of each derivative.

Tables 2, 2A and 3, 3A below show that the derivatives prepared according to the invention are much less toxic than amphotericine B for human and mice cells, and this can vary from derivative to derivative. Table 4 represents a comparative in vitro study of the toxicity of AmB, of the non-rearranged derivative, and of the same rearranged derivative using different catalysts.

In conclusion, these studies show that the derivatives obtained according to the present invention retain the antibiotic properties of AmB and that their toxicity has been completely lost or has diminished considerably.

TABLE 2

IN VITRO TOXICITY OF THE AmB DERIVATIVES FOR DIFFERENT MICE CELLS: COMPARISON OF THE SALTS OF DIFFERENT AmB DERIVATIVES.
LD 50 in molarity

| DERIVATIVES | RED CORPUSCLES | T LY. GL. CELLS+ | B LY. GL. CELLS+ |
|---|---|---|---|
| FUNGIZONE++ | $6 \times 10^{-6}$ | $1.5 \times 10^{-6}$ | $2 \times 10^{-6}$ |
| F SERIE | | | |
| AmB 12 | $2 \times 10^{-5}$ | $1 \times 10^{-5}$ | $1 \times 10^{-5}$ |
| AmB 17 | $3 \times 10^{-5}$ | $2 \times 10^{-5}$ | $1.5 \times 10^{-4}$ |
| AmB 20 | $1.2 \times 10^{-4}$ | $1 \times 10^{-4}$ | $1 \times 10^{-4}$ |
| AmB 22 | $9 \times 10^{-5}$ | $2 \times 10^{-5}$ | $2 \times 10^{-5}$ |
| AmB 23 | $1.2 \times 10^{-5}$ | N.D | N.D. |
| G SERIE | | | |
| AmB 12 | $2 \times 10^{-5}$ | N.D. | N.D. |
| AmB 17 | $1 \times 10^{-5}$ | N.D. | N.D. |
| AmB 20 | $4 \times 10^{-6}$ | N.D. | N.D. |
| AmB 22 | $1 \times 10^{-5}$ | N.D. | N.D. |
| AmB 23 | $4 \times 10^{-6}$ | N.D. | N.D. |

TABLE 2A

IN VITRO TOXICITY OF THE AmB DERIVATIVES FOR DIFFERENT MICE CELLS: COMPARISON OF THE SALTS OF DIFFERENT AmB DERIVATIVES.
LD 50 in molarity

| DERIVATIVES | THYMOCYTES | X 63** |
|---|---|---|
| FUNGIZONE++ | $2 \; 10^{-6}$ | $4 \; 10^{-5}$ |
| F SERIE | | |
| AmB 12 | $4 \times 10^{-6}$ | $>1 \times 10^{-3}$ |
| AmB 17 | $8 \times 10^{-6}$ | $>1 \times 10^{-3}$ |
| AmB 20 | $8 \times 10^{-6}$ | $>1 \times 10^{-3}$ |
| AmB 22 | $3.5 \times 10^{-6}$ | $>1 \times 10^{-3}$ |
| AmB 23 | $3 \times 10^{-6}$ | $>1 \times 10^{-3}$ |
| G SERIE | | |
| AmB 12 | $5 \times 10^{-6}$ | $5 \times 10^{-4}$ |
| AmB 17 | $5 \times 10^{-6}$ | $1.5 \times 10^{-4}$ |
| AmB 20 | $4 \times 10^{-6}$ | $1.5 \times 10^{-4}$ |
| AmB 22 | $5 \times 10^{-6}$ | $4 \times 10^{-4}$ |
| AmB 23 | $2.5 \times 10^{-6}$ | $5 \times 10^{-4}$ |

F SERIES: catalysis by oxlaic acid, NMG salt
G SERIES: catalysis by oxlaic acid, mixed ammonium and oxalate salt
+ly. gl.: paraaortic and inguinal lymph glands
**X 63: mice lymphoma B
++registered trademark

TABLE 3

IN VITRO TOXICITY OF THE AmB DERIVATIVES FOR DIFFERENT HUMAN CELLS: COMPARISON OF THE SALTS OF DIFFERENT AmB DERIVATIVES
LD 50 in molarity

| DERIVATIVES | PBL | RED CORPUSCLES | BONE MARROW |
|---|---|---|---|
| FUNGIZONE++ | $3.5 \times 10^{-5}$ | $3 \times 10^{-6}$ | $2 \times 10^{-4}$ |
| F SERIE | | | |
| AmB 12 | $>1 \times 10^{-3}$ | $1 \times 10^{-4}$ | $>1 \times 10^{-3}$ |
| AmB 17 | $>1 \times 10^{-3}$ | $2 \times 10^{-4}$ | $>1 \times 10^{-3}$ |
| AmB 20 | $>1 \times 10^{-3}$ | $2 \times 10^{-4}$ | $1 \times 10^{-3}$ |
| AmB 22 | $>1 \times 10^{-3}$ | $1 \times 10^{-4}$ | $1 \times 10^{-3}$ |
| AmB 23 | $8 \times 10^{-5}$ | $5 \times 10^{-5}$ | N.D. |
| G SERIE | | | |
| AmB 12 | $4.6 \times 10^{-5}$ | $3 \times 10^{-5}$ | N.D. |
| AmB 17 | $1 \times 10^{-5}$ | $5 \times 10^{-5}$ | N.D. |
| AmB 20 | $3 \times 10^{-5}$ | $8 \times 10^{-5}$ | N.D. |
| AmB 22 | $3 \times 10^{-5}$ | $5 \times 10^{-5}$ | N.D. |
| AmB 23 | $8 \times 10^{-6}$ | $1 \times 10^{-6}$ | N.D. |

TABLE 3A

IN VITRO TOXICITY OF THE AmB DERIVATIVES FOR DIFFERENT HUMAN CELLS: COMPARISON OF THE SALTS OF DIFFERENT AmB DERIVATIVES
LD 50 in molarity

| DERIVATIVES | THMOCYTES | DAUDI** |
|---|---|---|
| FUNGIZONE++ | $6 \times 10^{-5}$ | $2 \times 10^{-5}$ |
| F SERIE | | |
| AmB 12 | $>3 \times 10^{-4}$ | $>1 \times 10^{-3}$ |
| AmB 17 | $>3 \times 10^{-4}$ | $>1 \times 10^{-3}$ |
| AmB 20 | $>3 \times 10^{-4}$ | $>1 \times 10^{-3}$ |
| AmB 22 | $>3 \times 10^{-4}$ | $>1 \times 10^{-3}$ |
| AmB 23 | N.D. | $>1 \times 10^{-3}$ |
| G SERIE | | |
| AmB 12 | N.D. | $>3 \times 10^{-4}$ |
| AmB 17 | N.D. | $3 \times 10^{-4}$ |
| AmB 20 | N.D. | $5 \times 10^{-4}$ |
| AmB 22 | N.D. | $7 \times 10^{-4}$ |
| AmB 23 | N.D. | $3 \times 10^{-4}$ |

F SERIES: catalysis by oxlaic acid, NMG salt
G SERIES: catalysis by oxlaic acid, mixed ammonium and oxalate salt
**DAUDI: human lymphoma B
++registered trademark

TABLE 4

IN VITRO TOXICITY OF THE AmB 12 DERIVATIVE FOR HUMAN PBLS:
COMPARISON OF DIFFERENT CATALYSTS

| DERIVATIVE | LD 50 |
|---|---|
| FUNGIZONE++ | $3.5 \times 10^{-5}$ |
| Uncatalyzed[a] NMG salt | $8 \times 10^{-5}$ |
| Ethyl malonate[b] NMG salt | $>1 \times 10^{-3}$ |
| Oxalic acid[b] NMG salt | $>1 \times 10^{-3}$ |
| Acetic acid[b] | $2 \times 10^{-4}$ |

TABLE 4-continued

IN VITRO TOXICITY OF THE AmB 12 DERIVATIVE FOR HUMAN PBLS: COMPARISON OF DIFFERENT CATALYSTS

NMG salt (a) non-rearranged derivative
(b) catalyst used for the rearrangement
++ registered trademark

C) STUDY OF THE STRUCTURE AND STABILITY OF THE DERIVATIVES ACCORDING TO THE PRESENT INVENTION

C.1 Analytical study of the structure

C.1.a UV spectrum

The UV spectra of the AmB derivatives according to the invention show that the polyene structure of AmB is retained.

FIG. 1 shows the UV spectrum of AmB 12 F by way of example.

C.1.b Carbon NMR

The $^{13}C$ NMR spectra of the derivatives according to the invention confirm their Amadori structure.

Figure 2:
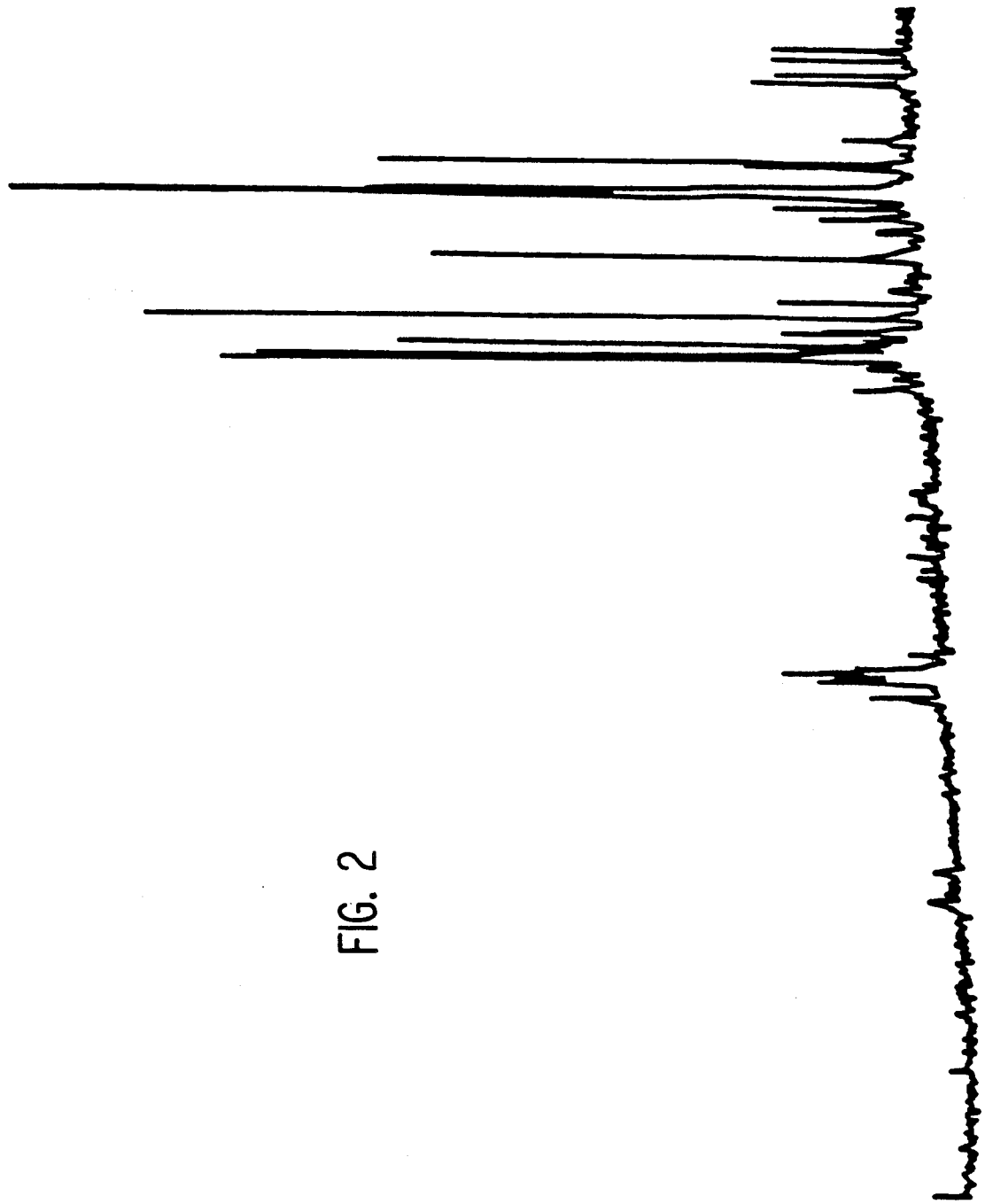
FIG. 2 shows the $^{13}$CNMR spectra of AmB 12 F.

The $^{13}C$ NMR spectra of AmB 12 F is shown by way of example in FIG. 2.

C.1.c HPLC

Figure 3A:
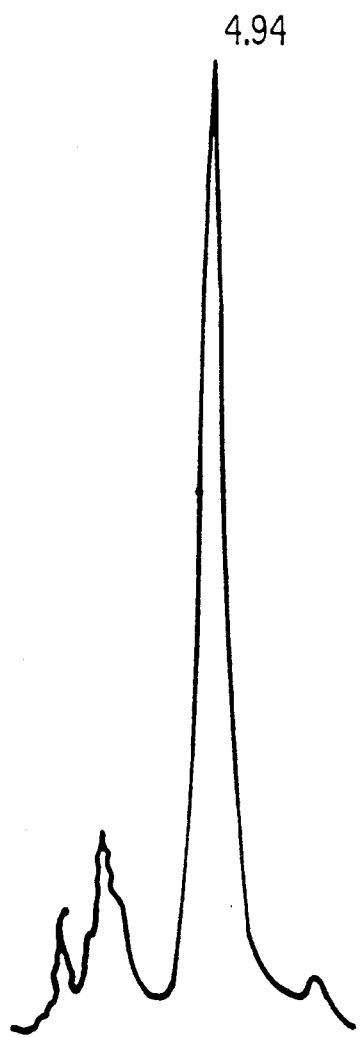
FIG. 3a shows the reverse phase HPLC spectra of the AmB derivative which is rearranged to produce rearranged AmB 12.
Figure 3B:
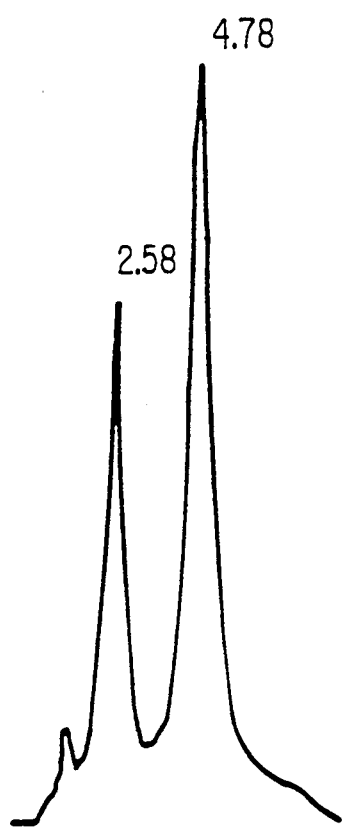
FIG. 3b shows the reverse phase HPLC spectra of the rearranged AmB 12.

FIG. 3 shows the reverse phase HPLC spectra of rearranged AmB 12 (3b) and of the corresponding non-rearranged derivative (32).

C.2. Solubility of the AmB derivatives according to the present invention

AmB or the derivatives obtained are dissolved at ambient temperature in a 5% glucose solution up to saturation.

Under these conditions, AmB is insoluble.

The AmB 17 derivative is soluble up to a concentration of 20 mg/ml.

The AmB 20 derivative is soluble up to a concentration of 40 mg/ml.

The AmB 12 derivative is soluble up to a concentration of 150 mg/ml.

C.3. Stability of the AmB derivatives according to the present invention

C.3.a : in solution

The decomposition of the derivatives over time is monitored by HPLC.

Figure 4:
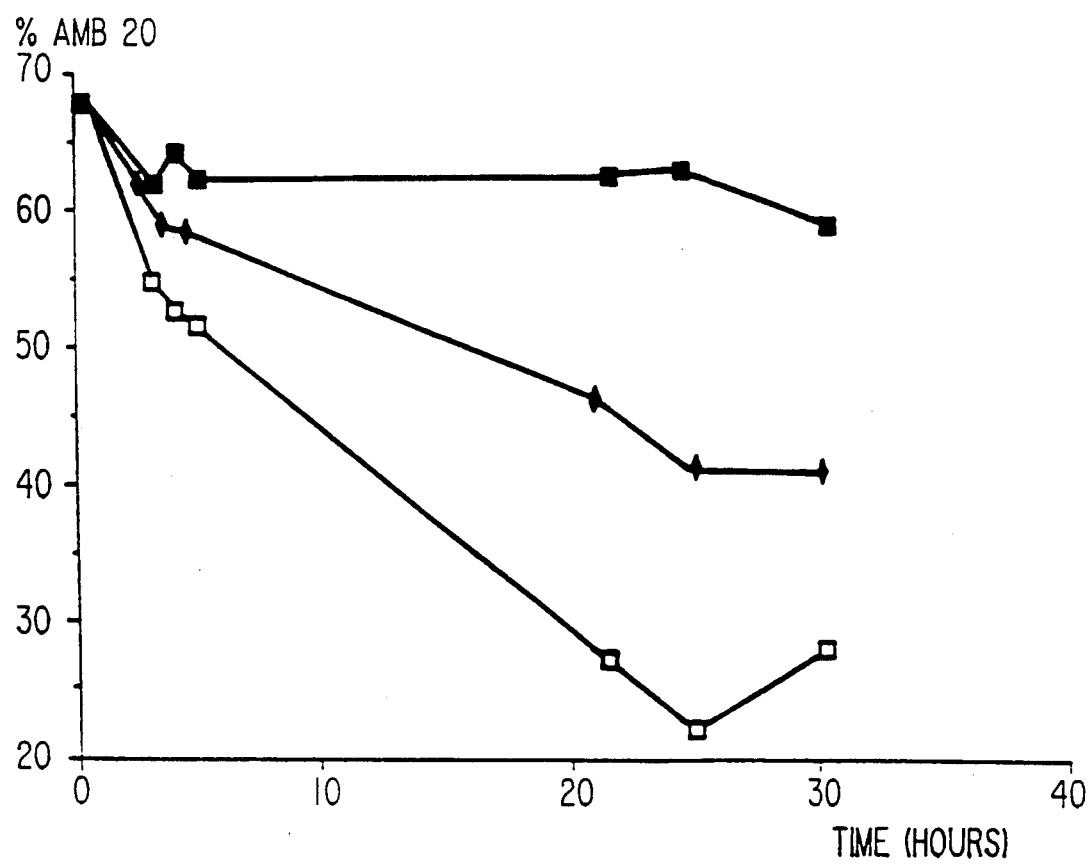
FIG. 4 shows the stability of the compound AmB 20, produced in Examples 5 and 6, at different temperatures.

FIG. 4 shows the results obtained (percentage of the non-decomposed derivative) with a 2.5 mg/ml solution of AmB 20 at
□ 37° C.
♦ ambient temperature
■ 4° C.

C.3.b. as a powder

When the derivatives according to the present invention are maintained in the form of a powder, they remain stable for several months.

We claim:

1. A basic polyene macrolide compound of the formula (I)

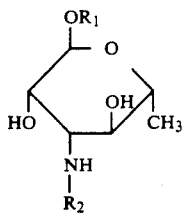

in which:

$R_1$ denotes the macrocylic part of amphotericin B and
$R_2$ represents a member selected from the group consisting of:

(1) a structure of the formula:

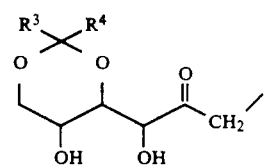

in which $R^3$ is selected from the group consisting of a hydrogen atom and a methyl group, and $R^4$ is selected from the group consisting of a hydrogen atom, a methyl, trichloromethyl, tert.-butyl, propyl, benzyl, phenyl group and a phenyl group substituted by a group selected from the group consisting of a methoxy, nitro and phosphate group, (2) - a structure of the formula:

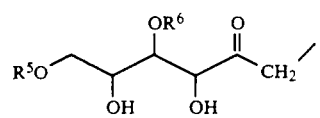

in which $R^5$ and $R^6$ are methyl groups, (3) - a structure of the formula:

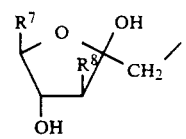

in which $R^7$ is selected from the group consisting of a carboxyl, amide, nitrile and trihalogenomethyl group, and $R^8$ is selected from the group consisting of a hydroxyl group, an amino group and a mercapto group, (4) - a structure of the formula:

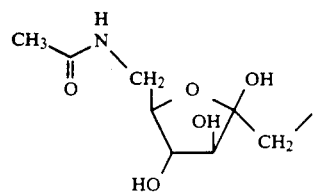

and a salt thereof, wherein said basic polyene macrolide compound being more soluble than the unsubstituted macrolide where $R_2$ in formula I is hydrogen.

2. The Brönsted acid salt of a compound of claim 2.

3. A compound of claim 2 which is a mixed oxalate and ammonium salt.

4. The N-methylglucosamine salt of a compound of claim 1.

5. A compound which is 1-amino-1-deoxy-D-arabinoglucuronyl-amphotericin B of the formula:

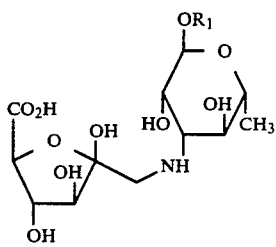

or its N-methylglucosamide salt, or its mixed oxalate and ammonium salt, where $R_1$ is the macrocyclic part of amphotericin B.

6. A compound which is 1-amino-1-deoxy-D-arabinoglucuroamidyl-amphotericin B of the formula:

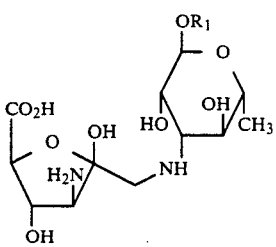

or its N-methylglucosamine salt, or its mixed oxalate and ammonium salt, where $R_1$ is the macrocyclic part of amphotericin B.

7. A compound which is 1-deoxy-1-amino-4,6-O-benzylidene-D-fructosyl-amphotericin B of the formula:

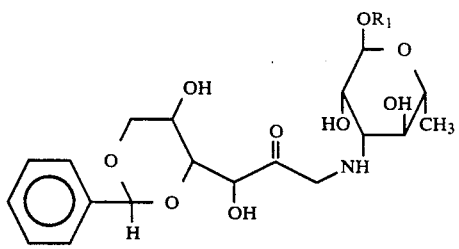

or its N-methylglucosamine salt, or its mixed oxalate and ammonium salt, wherein $R_1$ is the macrocyclic part of amphotericin B.

8. A fungicidal drug which comprises as the active principle in fungicidally effective amount a compound according to claim 1 in a pharmaceutically acceptable carrier.

9. A compound of the formula:

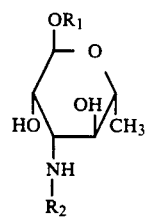

in which:
$R_1$ denotes the macrocyclic part of amphotericin B and
$R_2$ represents a 1-amino-1-deoxyketose group substituted by substitutent(s) selected from the group consisting of (1) a divalent group of the formula

replacing hydrogens of two different hydroxyl groups of the ketose, where $R^3$ is selected from the group consisting of a hydrogen atom and a methyl group, and $R^4$ is selected from the group consisting of a hydrogen, methyl, trichloromethyl, tert-butyl, propyl, benzyl, phenyl and phenyl substituted by a group selected from the group consisting of a methoxy, nitro and phosphate group, and (2) a monovalent group selected from the group consisting of methoxy, carboxyl, amide, nitrile, trihalogenomethyl, amine and mercapto group replacing a hydroxyl group of the ketose.

10. The N-methylglucosamine salt of 1-deoxy-1-amino-4,6-O-benzylidene-D-fructosyl-amphotericin B of the formula:

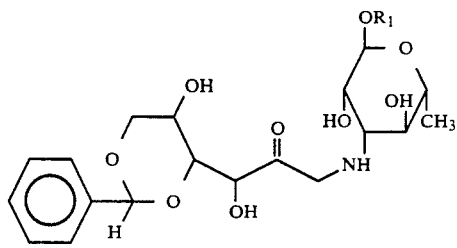

where $R_1$ is the macrocylic portion of amphotericin B.

11. The mixed oxalate-ammonium salt of 1-deoxy-1-amino-4,6-O-benzylidene-D-fructosyl amphotericin B of the formula:

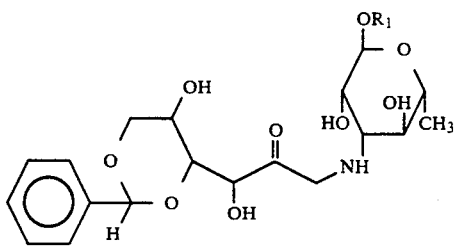

where $R_1$ is the macrocyclic part of amphotericin B.